United States Patent [19]

Deschler et al.

[11] Patent Number: 4,835,297

[45] Date of Patent: May 30, 1989

[54] METHOD OF PREPARING SULFENIC ACID CHLORIDES AND SULFENIC ACID ESTERS

[75] Inventors: Ulrich Deschler, Hanau; Rudolf Michel, Freigericht; Peter Kleinschmit, Hanau; Siegfried Wolff, Bornheim-Merten, all of Fed. Rep. of Germany

[73] Assignee: Degussa Aktiengesellschaft, Frankfurt/Main, Fed. Rep. of Germany

[21] Appl. No.: 940,069

[22] Filed: Dec. 10, 1986

[30] Foreign Application Priority Data

Dec. 10, 1985 [DE] Fed. Rep. of Germany ....... 3543567

[51] Int. Cl.$^4$ ............................. C07F 7/08; C07F 7/18
[52] U.S. Cl. .................................... 556/427; 556/428; 526/279; 524/262; 524/263
[58] Field of Search .......................................... 556/427

[56] References Cited

U.S. PATENT DOCUMENTS

| | | | |
|---|---|---|---|
| 3,842,111 | 10/1974 | Meyer-Simon | 556/427 |
| 4,278,585 | 7/1981 | Stacy | 556/427 X |
| 4,507,490 | 3/1983 | Panster | 556/427 |

*Primary Examiner*—Joseph L. Schofer
*Assistant Examiner*—Thomas McDonald
*Attorney, Agent, or Firm*—Cushman, Darby & Cushman

[57] ABSTRACT

The invention is directed to a method of preparing sulfenic acid chlorides and sulfenic acid esters with hydrolyzable silyl groups in which an oligosulfane containing silyl groups is chlorinated, the sulfenic acid chloride produced is separated and converted by reaction with an alkali alcoholate to the corresponding sulfenic acid ester.

5 Claims, No Drawings

METHOD OF PREPARING SULFENIC ACID CHLORIDES AND SULFENIC ACID ESTERS

BACKGROUND OF THE INVENTION

The invention is directed to a method of preparing sulfenic acid chlorides and sulfenic acid esters with hydrolyzable silyl groups.

German-OS No. 19 06 521 teaches a method of preparing sulfenic acid chlorides (sulfenyl chlorides) in which an unsaturated organosilane compound is reacted with sulfur dichloride. At the same time, however, there must be accepted the addition of chlorine to one of the C atoms of the originally unsaturated bond in the compound.

N. Auner and J. Grobe (Z. anorg. allg. Chem. 500, 1983, pp. 132–160, especially p. 153) describe a similar $SCl_2$-addition, which, however, starts with 1,3-silacyclobutanes, whereby a sulfenyl chloride with only one hydrolyzable group on the Si atom can be obtained. Stacy U.S. Pat. No. 4,278,585 is directed to sulfenic acid esters which are extracted by the esterification of sulfenic acid chlorides formed in the reaction of mercaptan containing silyl groups with sulfuryl chloride in the presence of amines.

This method has the disadvantage that there can only be obtained a product mixture which is contaminated by numerous by-products and which is difficult to separate. Furthermore the use of amines as HCl receptors results in precipitates which are difficult to filter.

Sulfenic acid chlorides and sulfenic acid esters with hydrolyzable silyl groups are used in the preparation of polymers which can be hardened with moisture or vulcanized or are used as reinforcing additives in rubber mixtures containing silica and cross-linked with sulfur.

The invention has the task of preparing the mentioned chlorides and esters in good yields and in the form of pure products.

SUMMARY OF THE INVENTION

The invention is directed to a method of preparing sulfenic acid chlorides and sulfenic acid esters with hydrolyzable silyl groups, characterized in that an oligosulfane containing silyl groups of the formula (I)

$$[(R)_b(R'O)_cSi-(CH_2)_n-]_2-S_x \text{ in which}$$

R is $C_1$–$C_2$ alkyl, especially methyl,
R' is $C_1$–$C_5$ alkyl (e.g. methyl, ethyl, butyl, amyl, sec butyl), $C_5$–$C_6$ cycloalkyl (e.g., cyclopentyl, cyclohexyl), especially methyl, ethyl, cyclohexyl, aralkyl, especially benzyl,
x is 2 or 3 or 4, preferably 2,
n is 1 or 3, preferably 3,
b is 0 or 1, preferably 0, and
c is 2 or 3, with b+c=3 is dissolved in an organic solvent which is inert to chlorine and this solution is treated slowly and with strong cooling with 2 to 6 times the molar amount of chlorine, based on the oligosulfane, stirred until a complete conversion to a sulfenic acid chloride having the composition given in formula (II):

$$Cl_a(R)_b(R'O)_dSi-(CH_2)_n-SCl,$$

in which a is 1 or 2 and d is 1 or 2 with a+b+d=3, and the other symbols are as defined above, the solvent and any sulfur chloride formed are removed in a vacuum, the accumulating raw product is fractionated in a vacuum, the purified sulfenic acid chloride (mixture) of formula (II) obtained in this manner is dissolved in an organic solvent, this solution is treated dropwise with vigorous agitation and, in a preferred embodiment, with the simultaneous introduction of nitrogen with the amount of an alcohol stoichiometric to a of formula (III)

$$R'OH$$

at a temperature of 0° to 60° C., the solvent removed after the esterification of the Si—Cl groups, the sulfenic acid chloride of formula (IV)

$$(R)_b(R'O)_cSi-(CH_2)_n-SCl$$

in which the symbols are as defined above is obtained by fractional distillation, this compound is dissolved in an inert solvent, the solution treated at 0° to 60° C., preferably at room temperature, with an equimolar amount of an alkali alcoholate of the formula (V)

$$R'OY$$

in which Y designates Na, K or Li, preferably dissolved in the corresponding alcohol R'OH, the precipitated alkali chloride is filtered off after the reaction, the solvent and the remaining alcohol drawn off and the sulfenic acid ester of formula (VI)

$$R_b(R'O)_cSi-(CH_2)_n-SOR'$$

is obtained.

The oligosulfanes according to formula (I) added in the first method step are readily accessible in high yields, e.g. according to the methods described in German PS No. 21 41 160 (and related Meyer-Simon U.S. Pat. No. 3,842,111), German OS No. 33 11 340 (and related Panster U.S. Pat. No. 4,507,490). During their reaction with elemental chlorine in solvents which are inert to chlorine, a splitting of the polysulfane chain occurs with formation of two sulfenic acid chloride functions. Since the formation of sulfur chlorides is observed in addition when trisulfanes and tetrasulfanes are used, the use of disulfanes (x=2 in formula (I)) is preferred, even though the sulfur chlorides can be easily separated by distillation. Aromatic hydrocarbons such as, for example, benzene, toluene, xylene or aliphatic hydrocarbons such as, for example, n-pentane, n-hexane and cylcohexane or partially chlorinated hydrocarbons, for example, methylene chloride, chloroform and carbon tetrachloride can be used as solvents which are inert to chlorine, especially at temperatures of ≦0° C. and in particular in the dark; however, carbon tetrachloride is preferred here and even more at an elevated temperature under the action of light. Chloroform is the preferred solvent only at temperatures below −23° C. and methylene chloride at temperatures below −64° C. Tetrahydrofuran, dioxane, diethyl ether and acetonitrile are also suitable. Elemental chlorine can be added to the reaction mixture dropwise in liquid form at reaction temperatures of >−100° C. to −35° C. or passed in a gaseous form through the reaction solution maintained at temperatures of −35° C. to +77° C. The invention also provides for the dropping of previously condensed chlorine maintained in a liquid state at temperatures of >−100° C. to −35° C. into a reaction mixture whose temperature is −35° C. to +77° C., preferably −10° C. to +10° C. For industrial reasons, it is preferable to pass gaseous chlorine at a temperature of 0° to 5° C. through the reaction solution since the partial chlorination of the alkoxy silyl groups can not be suppressed even at lower temperatures. On account of this partial formation of chlorosilyl groups, an excess of chlorine is required which is in the range of 1–5 moles, preferably 3 moles. Greater excesses of chlorine are useless since they leave the reaction medium again in unreacted form. A certain portion of sulfur chains remains in an unreacted form at less than a threefold excess of chlorine in relation to the oligosulfane (that is, 4 moles $Cl_2$ per mole of oligosulfane), which causes the yield of sulfenyl chlorides of formula (II) to be lowered in a corresponding manner. On account of the strong exothermy, the chlorinating reaction is preferably carried out in a diluted reaction medium with external cooling (in the laboratory, for example, with ice). However, it is also possible in principle to work without solvents. The degree of dilution by solvent is primarily determined by the design and capacity of the cooling system and is typically in the range of 250–500 ml/mole oligosulfane on a laboratory scale; however, other amounts of solvent can also be used in industrial and plant scale operation.

The working up of the mixture obtained in the chlorination reaction consists in a distillative separation of the solvent and of any by-products formed, such as, for example, $SCl_2$ or $S_2Cl_2$, which is performed advantageously at a subatmospheric pressure of 20–150 mbar and at room temperature. The raw product obtained thereby as distillation bottom, which is colored orange to deep red, can contain up to two individual constituents of the compounds given in formula (II), which differ from one another by a different degree of chlorination on the Si atom (that is, a=1 or 2), in addition to slight amounts of the initial silanes of formula (I). A fractional vacuum distillation of the raw product which is performed, for example, at subatmospheric pressures of 0.01–10 mbar is especially advantageous for the separation of these oligosulfanes. The main fraction obtained is one (a=1 or a=2) or also a mixture of the two sulfenyl chlorides of the composition represented by formula (II) which differ only slightly from one another in their boiling points. If a mixture is present, the magnitude of stoichiometric factor a must be determined by an analytical determination of the total chlorine (e.g. decomposition according to Schoninger, argentometric determination, potentiometric end-point indication) prior to the reesterification of the Si—Cl groups with an alcohol of formula (III).

In the second step of the reaction sequence of the invention the silane (mixture) of formula (II) is reacted with an amount of the alcohol of formula (III) which is precisely stoichiometric with respect to a and whose alkyl radical corresponds exactly to that of the alkoxy silyl group(s) in the silane(s) of formula (II).

This esterification reaction, known of itself, can be performed according to different methods such as, for example, that shown in German patent No. 20 61 189 with continuous processing or, for example, that in German patent No. 28 00 017 with discontinuous reaction. The only important consideration thereby is to avoid such stoichiometries and reaction conditions which could also result in the esterification of the S—Cl function.

An example of such conditions would be the dissolving of the sulfenic acid chlorides of formula (II) in an aprotic, organic solvent (aromatic/aliphatic hydrocarbons—(e.g. benzene, toluene, hexane, aromatic-/aliphatic chlorinated hydrocarbons e.g. chlorobenzene, methylene chloride, open-chain/cyclic ethers, e.g. diethyl ether, tetrahydrofuran, dioxane and ketones, e.g. acetone, dimethyl formamide, dimethyl sulfoxide) in the proportions of 250–500 ml per mole silane and the dropwise addition of the alcohol of formula (III) at temperatures of 0° to 60° C., whereby an inert gas (e.g. nitrogen) is allowed to flow through the reaction mixture in a preferred embodiment in order to rapidly remove the HCl gas formed as by-product.

If the isolated preparation of the sulfenyl chloride of formula (IV) is desired, then it is appropriate to work up the reaction mixture obtained after the esterification reaction in a known manner by distilling off the solvent and any other volatile components present in a vacuum. The crude product obtained in this manner has a high degree of purity (typically 92–97%), as can be demonstrated, for example, by elemental analysis, mass spectrometry or $^1$H-NMR spectroscopy. Sulfenyl chlorides of still greater purity can be obtained by a subsequent vacuum distillation, whereby the highest vacuum possible (under 1 mbar) should be maintained during the distillation.

In order to esterify the S—Cl function in the silanes of formula (IV), they are dissolved in an aprotic, organic solvent or the reaction solution obtained during the esterification of the Si—Cl bonds is immediately used without working up and isolation of the sulfenyl chlorides of formula (IV). Such solvents can be all those already mentioned above in the paragraph referring to the Meyer-Simon and Panster patents, whereby petroleum ether or toluene are preferred for economic reasons. The minimum amount of solvent used depends on its tendency to precipitate the alkali chloride formed during the reaction as by-product and, for example, is 150 ml per mole silane for aromatic or aliphatic hydrocarbons. Any greater amounts of solvent desired can be employed. The method of the invention for esterifying these sulfenyl chlorides of formula (IV) consists of treating their solution with the precisely equimolar amount of the alkali acoholate of formula (V) dissolved in alcohol of formula (III), whose alkyl radical corresponds to those of the alkoxy silyl groups in the silanes of formula (IV). The concentration of the alcoholic alcoholate solutions used should be as high as possible in order not to adversely affect as quantitative a precipitation as possible of the alkali chlorides formed as by-products (lithium chloride, for example, can be dissolved in alcohols, for which reason lithium alcoholates are less suitable as esterification agents and sodium alcoholates are preferred for this purpose). The upper concentration limit for these alcoholate solutions is determined by their viscosity at the temperature of addition and is at room temperature, for example, approximately 30 percent by weight for methylate and approximately 20 percent by weight for ethylate. These solutions can be prepared in a particularly simple manner by adding the appropriate amount of alkali metal to the alcohol, since, as is known, alkali alcoholate is formed thereby with development of hydrogen, which alkali alcoholate accumulates dissolved in the excess alcohol. However, it is also possible to simply stir commercially available alkali alcoholates such as sodium methylate as powdery solids into the appropriate alcohol. The esterification of the sulfenyl chloride function in silanes of formula (IV) with the aid of alkali alcoholates occurs spontaneously at room temperature (20°-25° C.) without excessively high evolution of heat. The operation is therefore preferably performed at this temperature; however, the same reaction is qualitatively observed at other temperatures.

The lower temperature limit depends on the freezing points of the particular solvents used and the upper limit on their boiling points. The temperature range which can be set with common solvents at a justifiable expense is between 0° C. and 60° C.

The isolation of the sulfenic acid esters of formula (VI) is carried out most simply by filtering off the alkali chloride precipitate formed according to known methods and by distillative removal of the solvent and the alcohol of formula (III) at normal pressure or in a vacuum. The raw products which accumulate as yellow liquid are very pure already (94-97% according to sulfur analysis), so that a vacuum distillation is not necessary.

The three-step method of the invention for preparing the sulfenic acid esters of formula (VI) has the following advantages over the one described in Stacy U.S. Pat. No. 4,278,585;

1. The oligosulfidic initial silanes of formula (I) are readily accessible in one step in high yields from 3-chloropropane silanes (e.g. German-OS No. 33 11 340 and the related Panster U.S. Pat. No. 4,507,490; 96% yield for the disulfide), while the 3-mercaptopropyl silanes used in Stacy U.S. Pat. No. 4,278,585 as silane additives can only be obtained in comparatively low yield in a one-step method starting with 3-chloropropane silanes (cf., for example, Great Britain Pat. No. 1,102,251: yield 43%) or requires a more expensive two-step method (cf., for example, German-PS No. 11 63 818: yield 67%).

2. The use of the oligosulfanes of formula (I) in accordance with the invention permits an easy distillative separation of the products of formula (II) in the event of incomplete conversion during the chlorination, since the particular molecular weight behave approximately as 2:1, wherewith great boiling point differences exist. In contrast thereto, there is only a slight difference of molecular weight and therewith of boiling point between the 3-mercaptopropyl silanes used in Stacy U.S. Pat. No. 4,278,585 and the 3-trialkoxysilylpropyl sulfenyl chlorides obtained therefrom, so that a distillative product separation and purification is not possible.

3. The esterification of the sulfenic acid chloride function is silanes of formula (IV) with the aid of alkali alcoholates in accordance with the invention has in particular the advantage over the variant described in Stacy U.S. Pat. No. 4,278,585, with the combined use of alcohols and tertiary amines (as HCl acceptors), that in this procedure of the invention only a readily filterable alkali chloride precipitate is formed, while in the Stacy procedure amine hydrochlorides are produced as voluminous precipitates which are difficult to filter off.

The sulfenic acid chlorides prepared in accordance with the invention are reacted with prepolymers which still have double bond portions. Products are then obtained which vulcanize or polymerize under the action of moisture.

The sulfenic acid chlorides as well as the sulfenic acid esters can also be used as reinforcing additive in rubbers which contain silica and which can be cross-linked with sulfur.

The process can comprise, consist essentially of or consist of the stated steps with the recited materials.

DETAILED DESCRIPTION

Example 1

Preparation of $Cl_2(OCH_3)Si—C_3H_6—S—Cl$: The written form $—C_3H_6—$ here as in all following examples stands for the trimethylene group $—CH_2—CH_2—CH_2—$.

162 grams of $(CH_3O)_3Si—C_3H_6—S_2—C_3H_6—Si(OCH_3)_3$ are dissolved in 200 ml of $CCl_4$. 75.2 ml of liquid chlorine is added drop by drop to this solution at 0° C. within 3 hours. Then, the reaction mixture is agitated for 1 hour at room temperature and subsequently the solvent is drawn off in a vacuum. The orange-colored raw product obtained (178 grams) is fractionated over a Vigreux column in a vacuum. The main fraction (boiling point (2 mm)=105°-112° C., 139 grams ≙ a yield of 69.9%) is a yellow-colored liquid with a $Cl_2$ content of 44.1% (theory: 44.4%).

Example 2

Preparation of $Cl_2(C_2H_5O)Si—C_3H_6—S—Cl$ from the disulfide:

475 grams of $(C_2H_5O)_3Si—C_3H_6—S_2C_3H_6—Si(OC_2H_5)_3$ are dissolved in 300 ml of $CCl_4$. Gaseous chlorine is introduced into this solution at 0° C. within 10 hours via a dip tube until the solution no longer absorbs chlorine and the latter escapes for the first time via the superpressure valve (approximately 320 grams chlorine). After thawing to room temperature and drawing off the solvent, 447 grams of a reddish brown liquid is obtained which according to gas chromatography analysis consists of 85.4 area % $Cl_2(C_2H_5O)Si—C_3H_6—S—Cl$ and 11.9 area % $Cl(C_2H_5O)_2Si—C_3H_6—S—Cl$ in addition to other volatile components (Cl value: 38%). 377 grams of a yellow liquid ( ≙ a yield of 74.2%) can be obtained therefrom as main fraction (boiling point (0.05 mm)=100°-106° C.) by fractionation in a vacuum. The Cl content of the main fraction was determined to be 41.4% (theory: 41.9% Cl).

Example 3

Preparation of $Cl_2(C_2H_5O)Si—C_3H_6—S—Cl$ from the tetrasulfide:

269.5 grams of $(C_2H_5O)_3Si—C_3H_6—S_4—C_3H_6—Si(OC_2H_5)_3$ reinforcing additive Si 69 ®, Degussa) are dissolved in 150 ml of $CCl_4$. 252 grams of chlorine are introduced into this solution at 0° C. within 11 hours until saturation and after the reaction mixture has warmed to room temperature, the solvent and the sulfur chlorides formed as by-products are drawn off in a vacuum. 231 grams of a deep red liquid is obtained which is subjected to a fractional vacuum distillation. The main fraction (boiling point (0.2 mm)=103°-109° C., 215 g ≙ a yield of 84.7%) is a bright yellow liquid with an S content of 12.1% (theory: 12.6%) and with a Cl content of 41.9% (corresponding to theory).

Example 4

Preparation of $(CH_3O)_3Si—C_3H_6—S—Cl$ from the silane prepared according to Example 1:

139 grams of $Cl_2(OCH_3)Si—C_3H_6—S—Cl$ are dissolved in petroleum ether and treated dropwise with 37.2 grams of methanol at room temperature within 2 hours at 5°-10° C. with vigorous agitation and the introduction of gaseous nitrogen under the liquid surface. After the solvent is drawn off a main fraction (boiling point (0.15 mm)=102°–105° C., 116.5 grams ≙ a yield of 87.1%) is obtained whose S content 13.2% (theory: 13.9%) and whose Cl content is 15.2% (theory 15.4%).

Example 5

Preparation of (C$_2$H$_5$O)$_3$Si—C$_3$H$_6$—S—Cl from the silane prepared according to Example 3:

215 grams of Cl$_2$(OC$_2$H$_5$)Si—C$_3$H$_6$—S—Cl are dissolved in 200 ml of petroleum ether and compounded with 78.3 grams of ethanol as described in Example 4. The main fraction of the vacuum fractionation carried out after drawing off the solvent (boiling point (0.5 mm)=112°–115° C., 209.5 g ≙ a yield of 90.7%) has a Cl value of 13.5% (theory: 13.0%) and an S content of 11.4% (theory: 11.8%).

Example 6

Preparation of (CH$_3$O)$_3$Si—C$_3$H$_6$—S—OCH$_3$ from the silane prepared in Example 4:

116.5 grams of (CH$_3$O)$_3$Si—C$_3$H$_6$—S—Cl are compounded in 150 ml of petroleum ether and treated at room temperature with 30 minutes with 90 grams of a 30% solution of sodium methylate in methanol. Filtration is performed on the precipitated sodium chloride and the filtrate is freed of solvent in a vacuum. 103 grams (≙ a yield of 90.2%) of a yellowish brown liquid are obtained which decomposes when a vacuum distillation is attempted. The raw product has a S content of 13.6% (theory: 14.2%).

Example 7

Preparation of (C$_2$H$_5$O)$_3$Si—C$_3$H$_6$—S—O—C$_2$H$_5$ from the silane prepared in Example 5:

In analogy to the method described in Example 6, 189.2 grams (≙ a yield of 87.3%) of a liquid colored orangish brown with an S content of 10.7% (theory: 11.4%) whose $^1$H-NMR spectrum is shown in FIG. 5 (60 MHz) are obtained from 209.5 grams of (C$_2$H$_5$O)$_3$Si—C$_3$H$_6$—S—Cl and 308 grams of a 17% sodium methylate solution in ethanol in 250 ml of petroleum ether as solvent after the workup.

Example 8

Comparison example from Stacy U.S. Pat. No. 4,278,585:

In accordance with Example III of the cited patent, 196 grams of mercaptopropyl trimethoxysilane were dissolved in 2 liters of n-pentane and 135 grams of sulfuryl chloride were added drop by drop to this solution at room temperature within 2 hours. The mixture was agitated for 20 more minutes and the solvent was drawn off from the clear reaction mixture obtained. The $^1$H-NMR spectrum of the orange-colored reaction product (219 grams) proves the presence of the initial silane in a concentration of approximately 65%. In addition, products were obtained in particular whose methoxy groups on the silicon were partially substituted by chlorine. The further reaction of this reaction mixture with methanol/triethylamine, as described in Example III of Stacy U.S. Pat. No. 4,278,585, does not result in the formation of a homogeneous sulfenic acid ester.

The entire disclosure of German priority application No. P 3543567.4 is hereby incorporated by reference.

We claim:

1. A method for the production of a sulfenic acid chloride or a sulfenic acid ester having hydrolyzable silyl groups comprising dissolving a silyl group containing oligosulfane of formula (I)

$$[(R)_b(R'O)_c Si—(CH_2)_n]_2—S_x$$

where
R is C$_1$-C$_2$ alkyl,
R' is C$_1$-C$_5$ alkyl, C$_5$-C$_6$-cycloalkyl or aralkyl,
X is 2, 3 or 4,
n is 1 or 3,
b is 0 or 1, and
c is 2 or 3 and
wherein
the total of b+c is 3 in an organic solvent inert to chlorine and treating this solution slowly with strong cooling with 2 to 6 fold the molar amount of chlorine based on the oligosulfane, stirring until the end of the reaction to form a sulfenic acid chloride having the composition of formula II $$Cl_a(R)_b(R'O)_d Si—(CH_2)_n—S—Cl$$

where
a is 1 or 2, d is 1 or 2 and a+b+d is 3,
removing the solvent in a vacuum, fractionating the crude product obtained in a vacuum, dissolving the thus obtained purified sulfenic acid chloride of formula (II) in an inert organic solvent,
under vigorous stirring treating this solution dropwise with an alcohol R'OH of formula (III) in the stoichiometric amount at a temperature of 0° to 60° C., drawing the solvent off after the esterification, obtaining the sulfenic acid chloride of formula (IV)

$$(R)_b(R'O)_c Si—(CH_2)_n—S—Cl$$

by fractional distillation,
dissolving this compound of formula (IV) in an inert, aprotic organic solvent,
treating the solution with an equimolar amount of an alkali alcoholate of formula (V)

$$R'OY$$

where Y is Na, K or Li and isolating the sulfenic acid ester of formula (VI)

$$(R)_b(R'O)_c Si—(CH_2)_n—SOR'$$

after filtering off the alkali chloride precipitate and removing the solvent in a vacuum.

2. A method according to claim 1 wherein R' is methyl, ethyl, C$_5$-C$_6$ cycloalkyl or benzyl.

3. A method according to claim 1 where R is methyl and R' is methyl or ethyl.

4. A method according to claim 1 where b is 0.

5. A method according to claim 4 where R' is methyl or ethyl.

* * * * *